United States Patent
Olsson et al.

(10) Patent No.: US 7,540,862 B2
(45) Date of Patent: Jun. 2, 2009

(54) METHOD OF APPLYING ELASTIC END PIECES TO AN ABSORBENT PRODUCT WEB AND ABSORBENT PRODUCT PRODUCED THEREBY

(75) Inventors: Ken Olsson, Västra Frölunda (SE); Marie Johansson, Mölnlycke (SE); Helena Corneliusson, Bohus (SE); Robert Kling, Skene (SE)

(73) Assignee: SCA Hygiene Products AB, Gothenburg (SE)

( * ) Notice: Subject to any disclaimer, the term of this patent is extended or adjusted under 35 U.S.C. 154(b) by 1343 days.

(21) Appl. No.: 10/402,991

(22) Filed: Apr. 1, 2003

(65) Prior Publication Data

US 2003/0230378 A1    Dec. 18, 2003

Related U.S. Application Data

(60) Provisional application No. 60/368,953, filed on Apr. 2, 2002.

(51) Int. Cl.
*A61F 13/15* (2006.01)
*A61F 13/20* (2006.01)
*B29C 65/00* (2006.01)
*B32B 37/00* (2006.01)
*B32B 38/04* (2006.01)

(52) U.S. Cl. .................... 604/385.3; 604/385.24; 604/393; 604/394; 156/164; 156/265

(58) Field of Classification Search ........... 604/385.03; 156/62.6
See application file for complete search history.

(56) References Cited

U.S. PATENT DOCUMENTS

| | | | | |
|---|---|---|---|---|
| 5,904,675 A * | 5/1999 | Laux et al. | ............. | 604/385.29 |
| 6,051,094 A | 4/2000 | Melbye et al. | | |
| 2003/0097110 A1* | 5/2003 | Erdman | .................... | 604/385.3 |

FOREIGN PATENT DOCUMENTS

| WO | 99/60967 A1 | 12/1999 |
|---|---|---|
| WO | 00/47152 A1 | 8/2000 |
| WO | 02/24131 A1 | 3/2002 |

\* cited by examiner

*Primary Examiner*—Tatyana Zalukaeva
*Assistant Examiner*—Melanie J Hand
(74) *Attorney, Agent, or Firm*—Buchanan Ingersoll & Rooney PC (57) ABSTRACT

Starting from an elastic material web and an absorbent product web, the method includes removing a first material piece from the elastic material web to provide a second material piece with an aperture and applying the first piece to a first portion of the absorbent product web. The second piece is supplied to a second application station and a section of the second piece is stretched and applied to a second portion of the absorbent product web. In this way an absorbent product with elastic waist portions is manufactured efficiently and with a minimum of waste.

17 Claims, 5 Drawing Sheets

METHOD OF APPLYING ELASTIC END PIECES TO AN ABSORBENT PRODUCT WEB AND ABSORBENT PRODUCT PRODUCED THEREBY

CROSS-REFERENCE TO RELATED APPLICATIONS

This application claims priority under 35 U.S.C. § 119 to U.S. Provisional Application No. 60/368,953, filed on Apr. 2, 2002.

FIELD OF THE INVENTION

The present invention relates to a method of applying elastic end pieces to end portions of an absorbent product web, said absorbent product web being used for producing an absorbent product for absorbing human exudate, such as a disposable diaper. In particular the invention relates to a method in which the elastic end piece at one end of the absorbent product has side flap members formed integrally therewith as a single strip, said side flap members allowing for releasable closure of an absorbent product around a user's waist.

The invention also relates to an absorbent product, which can be produced in accordance with the method of the invention.

BACKGROUND ART

Absorbent products such as disposable diapers typically have two end portions commonly termed waist portions. These each extend from one end edge of the absorbent product up to a central or crotch portion, and each of the portions may occupy about ⅓ of the length of the product.

Elastic material may be applied to absorbent product webs used for forming disposable absorbent diapers. Such elastic material may be applied in the rear waist portion and/or the front waist portion of the absorbent products which are to be produced from the absorbent product web.

WO-A-99/60967 discloses an elastically extensible waist region comprising a continuous belt together with side flaps which may be made elastic. The elasticity is provided by means of a layered structure consisting of a further elastic member, preferably laminated between layers of the absorbent product chassis. The elastic in the waist portion also extends continuously into an upper portion of the side flaps.

Elastic materials such as elastic laminates (i.e. a layer of elastic material laminated to at least one further non-elastic layer) are expensive compared to the majority of other materials in the product. Due to the high speed mass production techniques for absorbent products currently used, there is a constant effort to solve the problem of how to reduce not only the amount of material used but also the amount of waste of material.

The present invention seeks to overcome the above problems by a method of applying elastic material pieces to the waist portions of an absorbent product web, in both a cost-saving and efficient manner, whereby waste is also minimized.

SUMMARY

These and other objects are achieved by a method according to embodiments of the invention, in which end pieces formed from an elastic material web are applied to an absorbent product web in areas to be elastic or elasticated. In this regard a material web is considered to be an elastic material web in accordance with the invention if it can be elastically extended by more than 50% without substantial permanent strain, whereby substantial permanent strain is understood as being of the order of more than about 10 to 30% of the initial length at the first stretching.

An absorbent product web in accordance with embodiments of the invention should be understood to mean at least one, preferably continuous, web of top sheet or back sheet material which is passed along an absorbent product manufacturing line. When the elastic end pieces are applied to the absorbent product web in accordance with the method according to embodiments of the invention, the absorbent product web may comprise e.g. only the back sheet and/or top sheet material or it may comprise any number of additional elements added thereto during the course of production. For example, an absorbent product web may comprise a back sheet and/or top sheet together with an absorbent core and/or standing gathers, and/or leg elastics etc. Other items may also be added to comprise the absorbent product web. The application of the elastic end pieces to the absorbent product web in accordance with the invention may occur before, during or after the attachment of any items to the top and/or back sheet thereof.

BRIEF DESCRIPTION OF THE DRAWINGS

The invention will now be explained in more detail with reference to certain non-limiting embodiments thereof and with the aid of the accompanying drawings, in which.

DETAILED DESCRIPTION OF PREFERRED EMBODIMENTS

Figure 1:
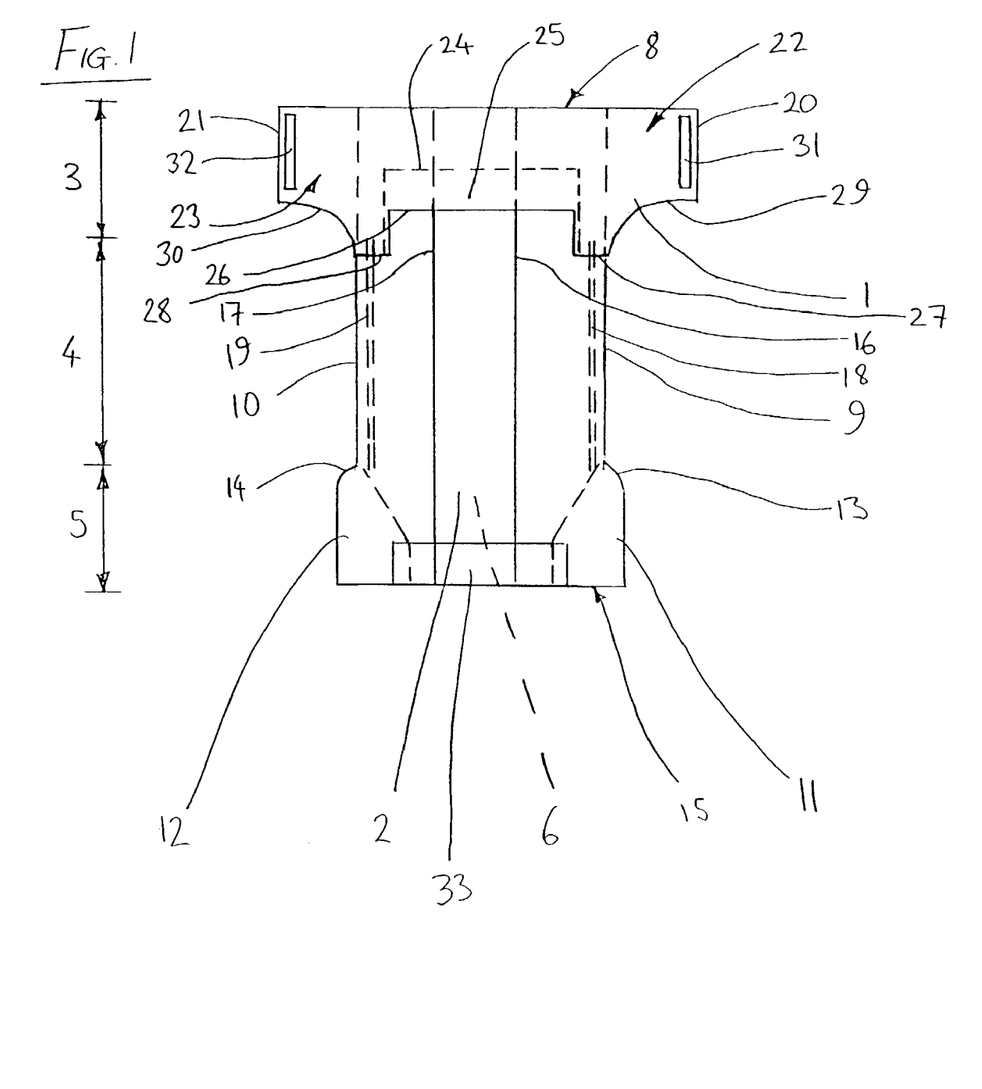
FIG. 1 shows one embodiment of an absorbent product produced by the method according to the invention.

In FIG. 1, an absorbent product in the form of a disposable absorbent diaper produced by the method of the invention is shown in plan view with the top sheet 2 of said product uppermost. The back sheet 6 is hidden in the view shown, but is however generally co-extensive with the top sheet 2, which has longitudinal side edges 9 and 10 extending longitudinally from end edge 8 (as shown in dotted lines underneath elastic end piece 1) down to curved portion 13, 14 of the top sheet and extending onward to end edge 15.

An absorbent core, not shown for reasons of clarity, may be positioned between the top sheet 2 and the back sheet 6 of the absorbent product.

The product has two end portions, a first end portion 5 and a second end portion 3, portions 5 and 3 being attached by means of a crotch portion 4. Second end portion 3 can be a rear end portion intended to lie in contact with the rear waist region of a wearer during use, while first end portion 5 can be a front end portion intended to lie in contact with the front waist region of a wearer during use. The product may however be worn such that the first end portion 5 and the second end portion 3 are inverted.

There is also no exact dimension for each of these portions, although it is generally understood that the crotch portion is that portion which is approximately longitudinally and transversely centrally located in the product. The crotch portion can be displaced longitudinally towards the first end portion 5.

The second end portion 3 can be provided with a continuous end piece 1, formed from elastic material. The elastic material is preferably a laminate having nonwoven material forming each outer surface with an elastic lamina between these.

The elastic material of the end piece 1 is preferably formed to have elasticity only in the transverse direction (i.e. side-to-side in FIG. 1) and thereby substantially no elasticity in the longitudinal direction. This is of advantage for example in improving the fit of the absorbent product to the back of the wearer, since gathering of the rear part of the product in a longitudinal direction is easily prevented.

The end piece 1 (as will be explained further below) is one symmetrical half of a second material piece section 61 (see FIG. 4), and overlies the other components of the absorbent product. In the embodiment shown, the end piece 1 overlies the combined top sheet 2 and back sheet 6, the standing gathers (of which the inner edges 16, 17 are depicted), the leg elastics 18, 19, as well as the absorbent core (not shown).

The end piece 1 of elastic material thus has a transverse end 8 extending from the outer edges 20, 21 of respective side flaps 22, 23, whereby the side flaps 22, 23 are to be understood as those portions of the continuous end piece 1 which extend beyond the longitudinal side edges 9, 10 at the second end portion 3.

The end piece 1 can be fixedly attached to the underlying elements of the absorbent product by means of adhesive or welding, or by any other suitable method.

In order to form a pocket cuff 25 in the absorbent article, to act as a barrier and containment pocket in particular for fecal matter, the end piece 1 is fixedly attached, while in a stretched condition, to the underlying components. However the attachment is preferably made only at locations which are longitudinally or laterally outside the dashed line 24. The inner, rectangular cut-out edge 26 of the pocket cuff 25 up to the line 24 is thus unattached to the underlying components.

The elastic material end piece 1 is preferably hydrophobic in order to function so as to contain fluids within the pocket cuff 25. However, it is undesirable to continue the elastic end piece 1 in the central part of the product 4 all the way down to the inner end edges 27, 28 of the end piece 1, since too great an area of the wearer may be juxtaposed to the hydrophobic layer and this may lead to leakage, especially when the wearer is lying on his/her back. Thus the rectangular cut-out indicated by edge 26 is provided in order to leave sufficient material remaining in the end piece 1 for forming the leg cut-outs 29, 30, but at the same time providing a recessed pocket cuff 25 which is less likely to result in leakage problems.

Releasable attachment means 31, 32, preferably of the mechanical fastening type such as hook-and-loop type fastening means (such as Velcro® for example) can be provided on the side flaps 22, 23. Such releasable attachments are well known to the skilled person and thus no further detailed description is provided here. These are adapted to releasably attach to complementary portions 11, 12 provided on the back sheet 6 of the first end portion 5 of the product. The portions 11 and 12 cover the corner areas of the back sheet 6 and have inner margins shown with partly slanted dashed lines ending in shorter longitudinal sections just inside the edges of piece 33. Such releasable attachment of the complementary releasable attachment means in the end portions may be made, in a manner known per se, after the absorbent product has been passed through the legs of a wearer in order to locate the crotch portion 4 in alignment with the user's crotch.

At the first end portion 5, there is a further elastic end piece 33 in the form of a rectangular strip. Other shapes of strip are however also possible such as a half-oval shaped strip for example. This end piece 33 is placed, in the embodiment shown, on top of all the components in the first end region 5, namely on top of the standing gathers and the top sheet in the first end region 5.

The end piece 33 is one symmetrical half of a larger, rectangular, first material piece (to be described further below) and may be applied to the absorbent product web in a stretched or unstretched condition. When applied in a stretched condition, which is the preferred case, the piece 33 will function so as to provide an elasticated waist region. However, when applied in an unstretched condition, the piece 33 will still function to provide comfort-enhancing properties.

In the embodiment shown, the end pieces 1 and 33 have both been applied in a stretched condition and thus the dimensions of end piece 33 will substantially correspond to those of the rectangular cut-out denoted by line 26 when the amount of stretching of end piece 1 and end piece 33 at attachment is equal and when the underlying substrate (e.g. web 56) presents the same stiffness resistance. In the unstretched condition of the end pieces, i.e. the relaxed condition, the dimensions of the end piece 33 will be substantially identical to that of the rectangular cut-out 26 (since end piece 33 is cut from end piece 1, as explained below).

In the preferred embodiment described above, although the end piece 33 is placed above the top sheet 2, the end piece 33 could also be attached to the back sheet 6 (e.g. on its outwardly facing side), or between the top sheet 2 and back sheet 6.

The product of the invention formed for example as shown in FIG. 1 thus has a first end portion 5 having an elastic end piece 1, which can suitably be termed a first elastic end piece 1, stretched and attached thereto. Similarly the second end portion 3 has a second elastic end piece 33 attached thereto, after having preferably been stretched. The first elastic end piece 1 includes an inner edge (i.e. an edge which is longitudinally inward in relation to the transversely extending end edges 8, 15 at either longitudinal end of the product), the inner edge being formed by portions 27, 28. The cut-out 26 which is preferably rectangular, joins these portions 27, 28 to form a recessed inner edge portion. Similarly, the second elastic end piece 33 is formed as a strip having dimensions equal to those of the cut-out 26. As explained above, the dimensions of the second elastic end piece 33 will be the same as those of the cut-out 26 when both the first elastic end piece 1 and the second elastic end piece 33 are in an unstretched condition.

The method of applying elastic end pieces in the form of a first material piece 44, and a second material piece section 61, and of forming the final absorbent product with attached first and second elastic end pieces (such as end pieces 1 and 33) will now be described with reference to FIGS. 2 to 5.

Figure 2:
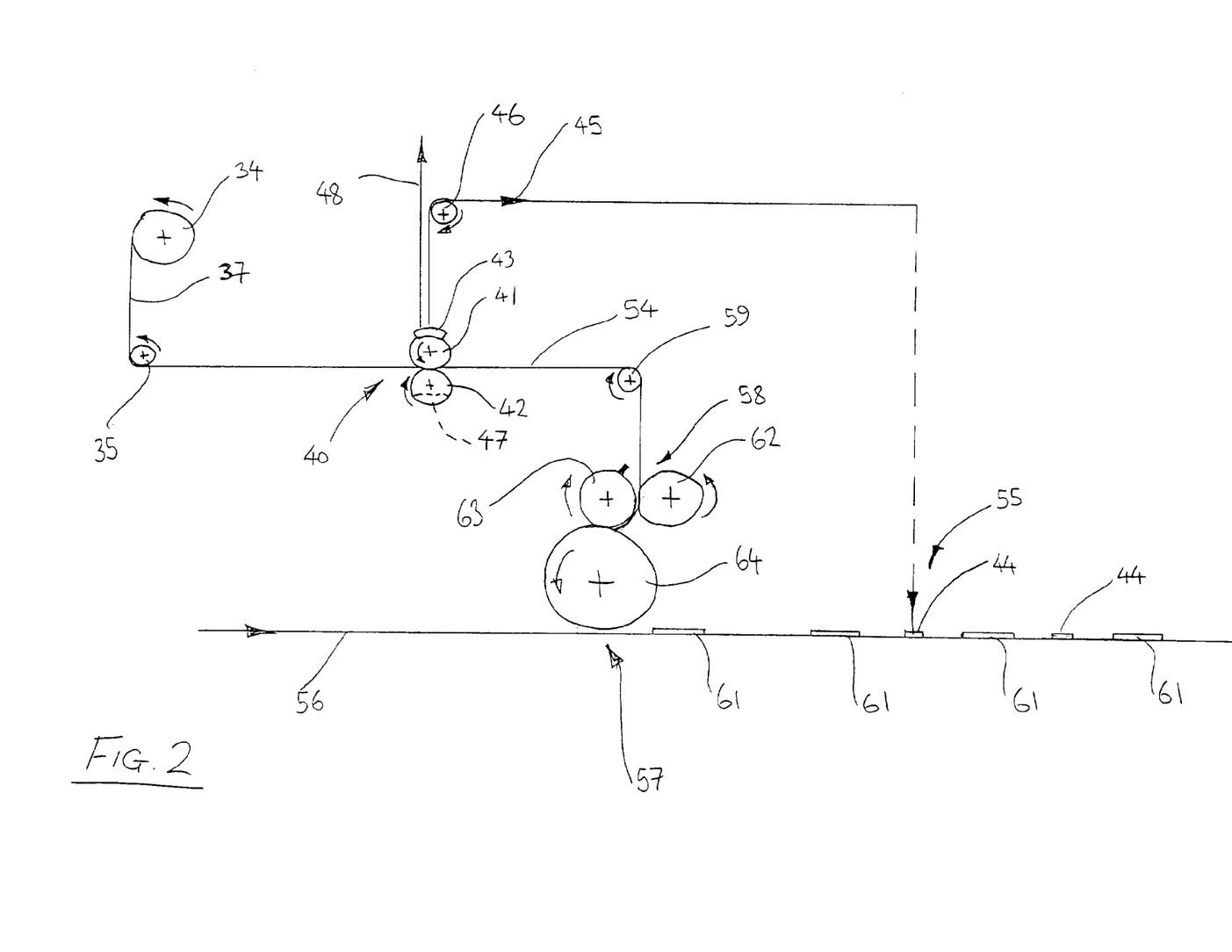
FIG. 2 shows a schematic representation of the various steps involved with the method of the invention.
Figure 3:
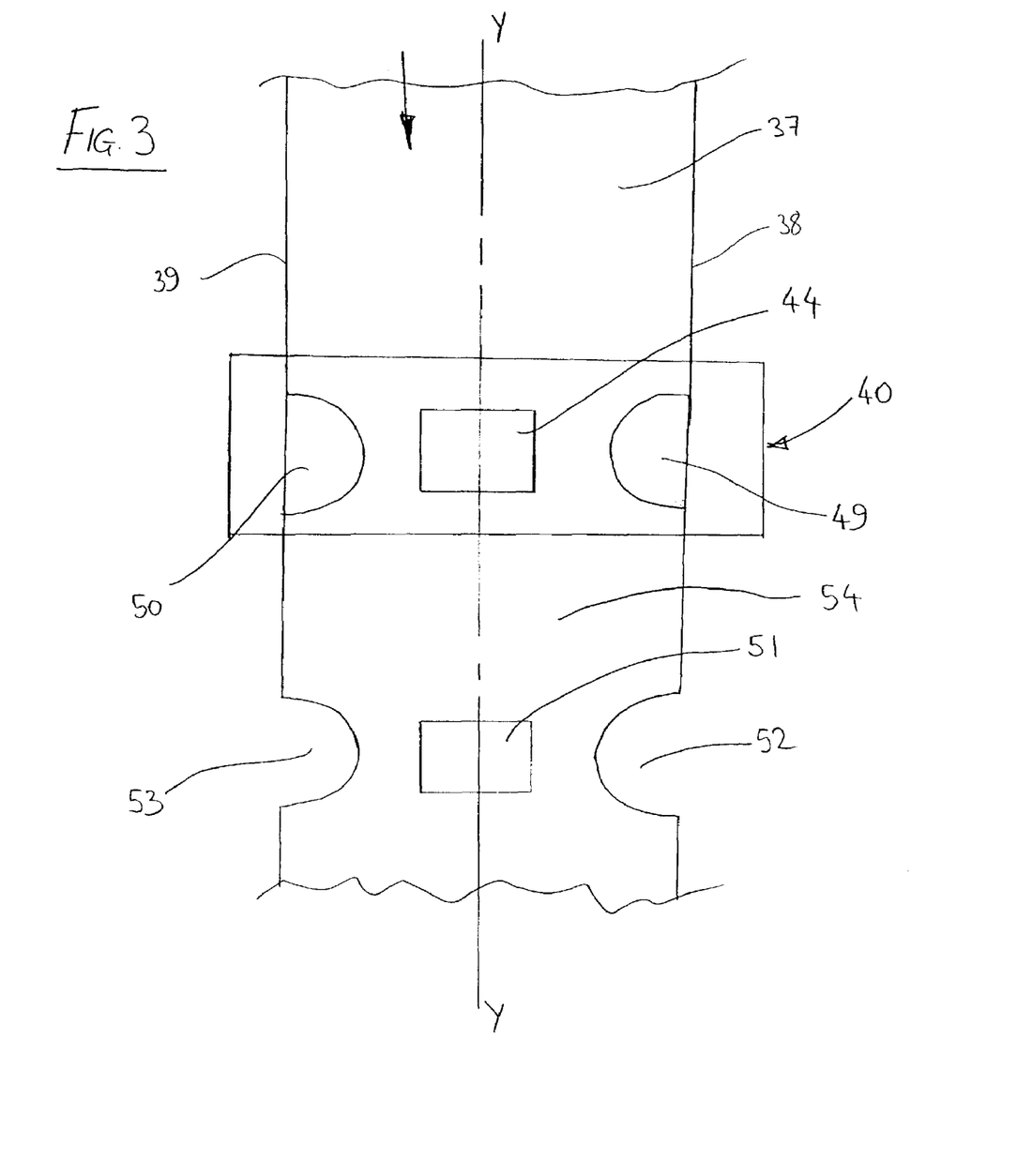
FIG. 3 shows, in plan view, the elastic material web entering into a station at which a first rectangular material piece is removed and two edge pieces, and the resultant second material piece exiting from the station.

FIG. 2 shows a schematic representation of the elements used in the method of the invention. Thus it will be understood that further, or different, components may be included than those described below. A product supply roll 34 containing an elastic material web 37 is depicted in the upper left corner. The elastic material web 37 preferably has elasticity only in the transverse direction. The web 37 is shown e.g. in FIG. 3, whereby the distance between the longitudinal side edges 38 and 39 of the web 37 is substantially constant and whereby the web has a generally longitudinal axis Y-Y midway between, and generally parallel to, the longitudinal side edges 38, 39.

The preferably continuous web 37 is unwound from supply roll 34 and fed around a first tensioning and/or guide and/or feed roller 35, towards a cutting station 40. The cutting station 40 may comprise for example a roller 41 fitted with a cutting and removal portion 43, and a counter roller 42. Counter roller 42 may have a surface which is able to bear against the cutting and removal portion 43 to allow cutting of the web 37, or counter roller 42 may for example be provided with a recess 47 allowing the cutter 43 to engage therewith. Instead of a pair of rollers, other cutting devices may be used, such as a stamping cutter.

In cutting station 40 a first material piece 44 is removed from the web 37. As shown, the piece 44 is removed from a location which is substantially centrally placed between the longitudinal side edges 38, 39 of the web 37.

The first material piece 44 is preferably rectangular, although other shapes are possible. The rectangular shape may also include rounded corners or slightly curved edges whilst still presenting a generally rectangular shape. From the first material piece 44 two equally sized second elastic end pieces 33 will be formed as explained below, such that the shape of the second elastic end pieces is determined by one substantially symmetrical half of the first material piece 44.

The cutting device 43 also functions, in the embodiment shown in FIG. 2, as a removing device whereby the first material piece 44 is fed away from the cutting station 40 along a conveyor 45. Conveyor 45 may for example be formed as a suction conveyor, whereby first material piece 44 would be held by means of suction to the conveyor 45 surface. Conveyor 45 is hereby shown passing around a further roller 46, such as a guide roller.

Two further material pieces 49, 50 located at respective longitudinal side edges 38, 39 are also removed, preferably at cutting station 40. The pieces 49 and 50 are removed for forming curved upper parts of leg cut-out portions 29, 30 in the final product. The pieces 49, 50 do not however need to be removed at cutting station 40 but instead may be removed upstream or downstream of station 40 by any suitable cutting device.

In the embodiment shown, the pieces 49, 50 are removed at station 40 and fed, to e.g. a waste container, along a path 48.

The first material pieces 44 are fed along conveyor 45 to a first application station 55 for application to an absorbent product web 56.

By removal of first material piece 44 at cutting station 40, the material web thus comprises an aperture 51. The material web 37 exiting the cutting station 40 and containing the aperture 51 will be referred to as a second material piece 54. The second material piece 54 is thus still in the form of a single web, but comprises an aperture 51. The second material piece 54 may also contain the further apertures 52, 53, if already formed at that stage.

As will also be clear from the following, the aperture 51 corresponds to double the size of a cut out portion 26 in the first elastic end portion 1 described above.

An absorbent product web 56, is fed by means (not shown) from left to right in FIG. 2. Absorbent product web 56 is fed through both a second application station 57 and a first application station 55. Although the first application station 55 is shown downstream of the second application station 57, it may equally be placed upstream thereof.

After exiting the cutting station 40, the second material piece 54 is diverted by guide roller 59 to a third station 58 comprising a further cutting device 63 and a slip device 62.

The purpose of the cutting device 63 is to cut the second material piece web transversely at successive locations 60 (see also FIG. 4) which are substantially midway across the aperture(s) 51. The slip device 62 has the purpose of forming a separation in the direction of arrows "A" between the second material piece 54 and a second material piece section 61 cut from said second material piece 54.

Figure 4:
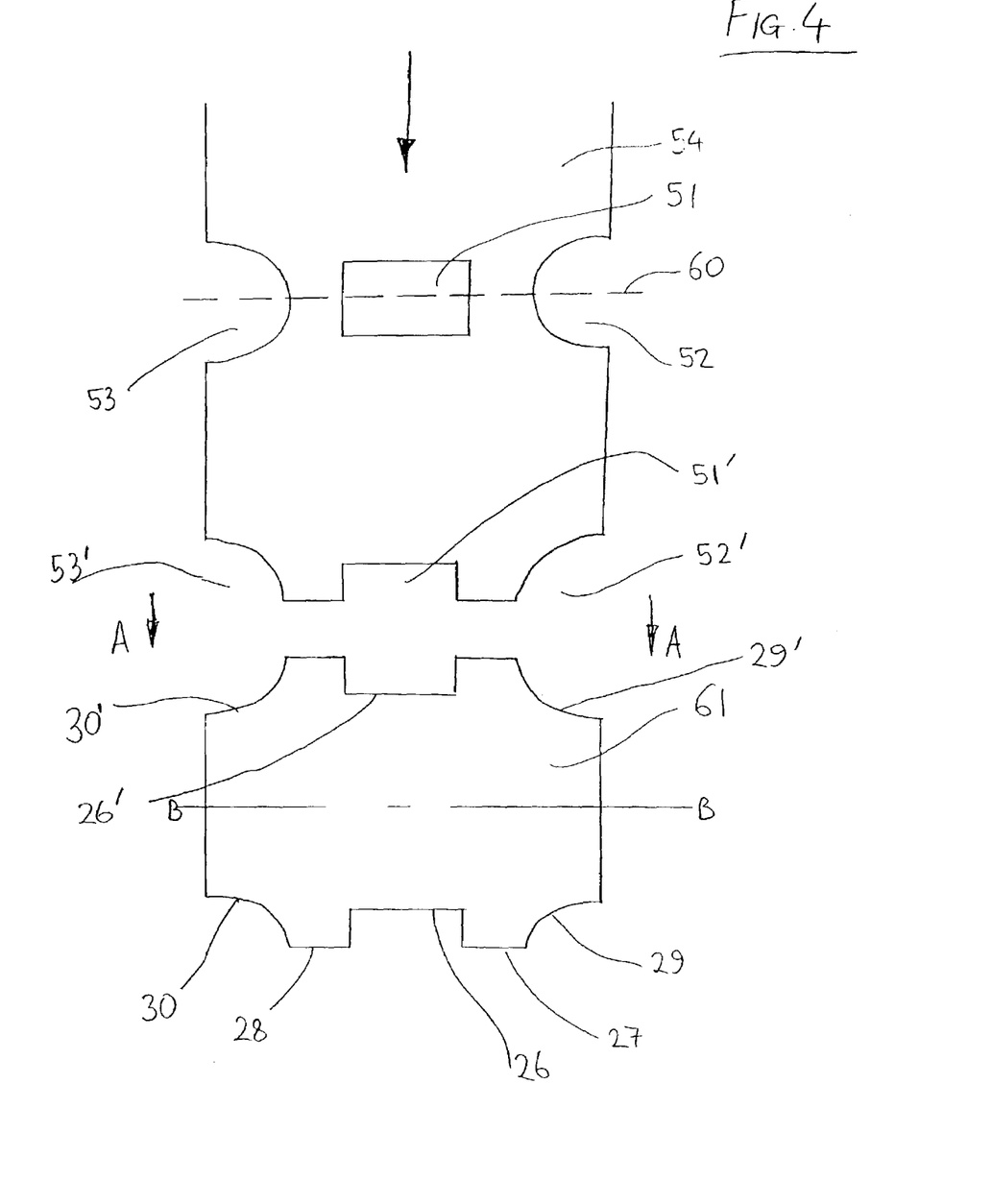
FIG. 4 shows a stage following that in FIG. 3, whereby the second material piece is cut so as to form a series of second material piece sections which are separated from one another.

As will be apparent from FIG. 4, the second material piece section 61 corresponds to two first elastic end pieces 1 (shown in FIG. 1) placed back-to-back across a line of symmetry B-B. The leg cut-outs 29, 30 and rectangular cut-outs 26 thus comprise half of the apertures 52, 53 and 51 respectively, while the cut-outs 29', 30' and 26' are half of the next set of apertures 52', 53', and 51'.

From the condition shown in FIG. 4, the second material piece section 61 must then be stretched before being applied to the absorbent product web 56. In order to do this, the second material piece section 61 is transferred to a stretching device 64, which in the embodiment shown simultaneously rotates and stretches the section 61 before applying same to the absorbent product web in a stretched condition at the second application station 57. Suitable means (not shown) are used for fixedly securing the section 61 in said stretched condition to the absorbent product web 56. Such means may comprise adhesive application means, welding means such as an ultrasound welding device, or any other suitable device which can provide a fixed attachment of the section 61 to the absorbent product web 56.

The section 61 comprises both a middle section and two end portions, whereby the end portions form side flaps 22, 23 in the waist region. Since the elastic material of the side flaps does not need to be attached to any further underlying non-elastic material in the embodiment shown, an advantage in handling and reliability is obtained in the methods according to embodiments of the invention when attaching the elastic section 61 to the absorbent product web 56 only at its transverse central region. This is because the section 61 only needs to be stretched by an amount sufficient for providing elasticity in the waist band area, thus by an amount of typically between 25 and 75%. Therefore, even though the side flaps 22, 23 may require to be extended by an amount between 100% and 200% or more (and in some cases even greater extensions of up to 300% or more), it is sufficient that just the section 61 is stretched, e.g. by between 25% and 75%, when being applied to the web 56, resulting in relatively low forces acting to remove the elastic section 61 from the device 64 and from the absorbent web 56 after application and attachment. This method may be contrasted with prior art attempts at producing elasticated waist areas, in which elastic material in one piece is stretched by amounts up to or over 200%, over all of its length, and then applied to both a non-elastic waist region and non-elastic side flap regions in order to elasticate the side flaps to the required amount, even though the waist region need not be elasticated by the same amount.

Figure 5:
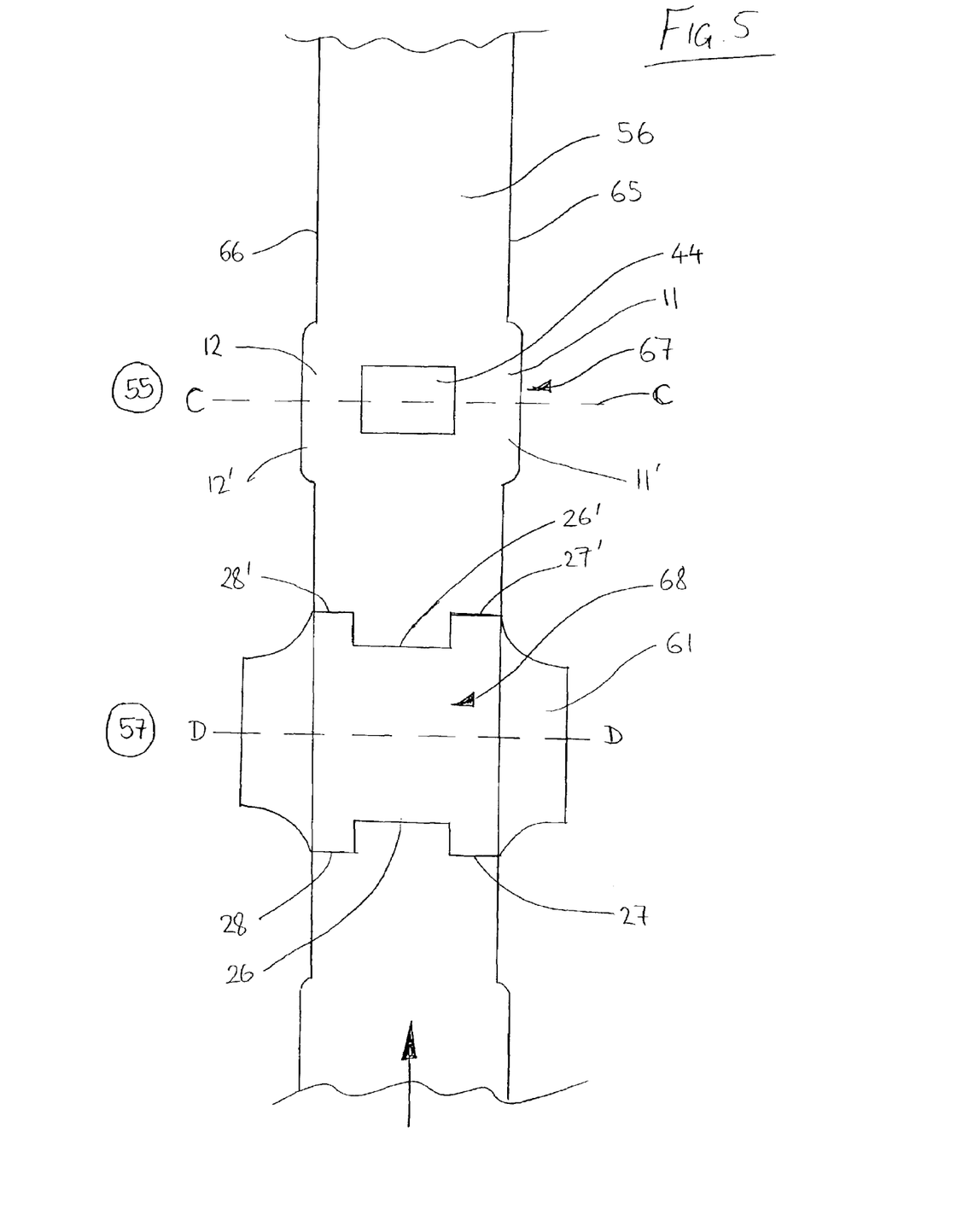
FIG. 5 shows a further stage following that shown in FIG. 4, whereby one second material piece section and one first material piece are applied to an absorbent product web.

FIG. 5 shows a plan view of the absorbent product web 56, whereby components such as standing gathers, leg elastics 18, 19 etc., have not been shown so as to aid clarity of the Figure. One or more of these components may however be present.

The web 56 has two longitudinal side edges 65 and 66. These longitudinal side edges correspond to, and will form, the longitudinal side edges 9, 10 of the absorbent product shown in FIG. 1.

The first material piece 44 is applied, and fixedly attached, preferably in a stretched condition of between 25% and 75% elongation, to a first end portion 67 (e.g., the first, single, end portion 5 in FIG. 1) of the absorbent product web 56. The first end portion 67 of the web 56 in the embodiment shown comprises the first or front waist end portions of two adjacent absorbent products. The material piece 44 is thus placed substantially symmetrically across a line of intended separation C-C. The reference numerals 11, 11' and 12, 12' are inserted to show, with respect to FIG. 1 for example, where the complementary attachment portions 11, 12 would be located on one side of line C-C.

Similarly, section 61 is applied, and fixedly attached in a stretched condition, to a second portion 68 of said absorbent product web 56 which second portion 68 is located at the second waist end portions (e.g., the second, single, end portion 3 in FIG. 1) of two adjacent absorbent products. The section 61 is attached symmetrically with respect to the intended line of separation D-D between two absorbent product second waist end portions.

The location of the attachment is such that an inner transverse end section of the second material section on either side of the line D-D will be unattached to the absorbent product web 56 over only a part of its longitudinal extent. This attachment is also shown clearly by means of line 24 in FIG. 1. In this way, a pocket cuff 25 will be suitably formed in each of the adjacent absorbent products.

The final absorbent products are produced by cutting all the way along the lines C-C and D-D through the absorbent product web 56 and the section 61 and the first material piece 44. As the result of each single cut, two substantially identical elastic waist sections are formed, one on one product and one on the adjacent product. In this way, the end edges of the final product formed where lines C-C and D-D are located, will each be a substantially flush joint edge, one flush edge being formed between one half of the first material piece 44 and the underlying product web 56 and the other being formed between one half of the section 61 and the underlying product web 56.

While in the presently preferred embodiments it has been described that the first material piece 44 and section 61 are attached to the absorbent product web 56 across adjacent waist end portions formed as a type of "dual" waist portion, in certain embodiments either the first material piece 44 and/or the second material piece 61 may be separated into two pieces before being applied to their respective ends. For example, if it is desired not to have the waist elastic piece 33 flush with the outer edge 15 of the first waist portion 5, it may be suitable to split the piece 44 into two pieces at an earlier station before the first application station 55 and then apply these separate pieces to the absorbent product web 56 at a location respectively displaced from the lines C-C and D-D of intended separation.

Similarly, if the products are not be produced front/front and back/back as in the shown embodiments, it will be preferable to split each of the first-material piece 44 and the section 61 into two pieces for respective application to the appropriate part of the products. Nevertheless, certain advantages of the invention still apply since minimum wastage of the available elastic material occurs due to the use of material piece 44 taken from an area of the second material piece 54 in an area of the second material piece 54 where it would otherwise be removed and discarded.

The releasable fastening means 31, 32 may be attached appropriately to the section 61.

Further embodiments will be readily understood by the skilled person upon reading the aforegoing and are intended to be encompassed within the scope of the invention as defined by the appended claims.

The invention claimed is:

1. A method of applying elastic end pieces to an absorbent product web, starting from an elastic material web having longitudinal side edges and a longitudinal central axis, and an absorbent product web, the method comprising the steps of:
    removing at least one first material piece from said elastic material web at a location within said longitudinal side edges of said web so as to provide a second material piece with at least one aperture therein;
    feeding said first material piece to a first application station and applying said first material piece to a first portion of said absorbent product web, said first portion being located at a first end portion of at least one absorbent product of said absorbent product web; and
    feeding said second material piece to a second application station and applying a section of said second material piece in a stretched condition to a second portion of said absorbent product web, said second portion being located at a second end portion of at least one absorbent product of said absorbent product web.

2. The method according to claim 1, wherein said first material piece is substantially rectangular.

3. The method according to claim 1, wherein said aperture is located centrally between said longitudinal side edges.

4. The method according to claim 1, wherein said first material piece is applied in a stretched condition to said first portion.

5. The method according to claim 1, wherein said first material piece is applied in a non-stretched condition to said first portion.

6. The method according to claim 1, wherein the first application station is downstream of the second application station.

7. The method according to claim 1, wherein said second portion is located at a second waist end portion of two adjacent absorbent products, and wherein said second material piece section is placed symmetrically across an intended separation line between said two adjacent absorbent products.

8. The method according to claim 1, wherein said first portion is located at a respective first waist end portion of two adjacent absorbent products, and wherein said first material piece is placed symmetrically across an intended separation line between said adjacent absorbent products.

9. The method according to claim 1, wherein said absorbent product web has longitudinal side edges and wherein said second material piece section is applied to said absorbent product web such that portions of said second material piece section extend beyond the respective longitudinal side edges of said absorbent product web to thereby form side flap members.

10. The method according to claim 9, wherein said second material piece section is applied to said second portion by being stretched between 25% and 75% and then being attached to said second portion in said stretched condition.

11. The method according to claim 1, wherein a further material piece is removed at each longitudinal side edge of said second material piece or said elastic material web, in longitudinal alignment with said at least one aperture, prior to the application of said second material piece section to said absorbent product web, so as to form leg cut-out areas in said second material piece.

12. The method according to claim 1, wherein subsequent to removal of at least one of said first material pieces, said second material piece is fed to a third station for cutting said second material piece into said second material piece sections, said cutting being performed in a transverse direction with respect to the longitudinal side edges of said second material piece and at locations bisecting said aperture, and then separating said second material piece sections from each other before stretching and applying the separated second material piece sections to said absorbent product web.

13. The method according to claim 1, wherein said second material piece section is applied to said absorbent product web so as to be fixedly attached thereto, such that with respect to absorbent products intended to be formed from said absorbent product web, an inner transverse end section of said second material piece section is unattached to the absorbent product web over only a part of its longitudinal extent and only a part of its transverse extent to thereby form a pocket cuff.

14. The method according to claim 1, wherein releasable fastening means are fixedly attached to said second material piece section at longitudinal side edges thereof so as to provide releasable attachment means for cooperating with releasable fastening means located on said first portion.

15. The method according to claim 1, wherein, subsequent to the application of at least one of said first material pieces and at least one of said second material piece sections to said absorbent product web, said absorbent product web is separated into a plurality of absorbent products by cutting transversely with respect to the longitudinal side edges of said absorbent product web at a location generally bisecting said first material pieces and at a location generally bisecting said second material piece sections.

16. The method according to claim 1, wherein the elastic material web has elasticity only in the transverse direction.

17. A method of applying elastic end pieces to an absorbent product web, starting from an elastic material web having longitudinal side edges and a longitudinal central axis, and an absorbent product web, the method comprising the steps of:
removing at least one first material piece from said elastic material web at a location within said longitudinal side edges of said web so as to provide a second material piece with at least one aperture therein;
feeding said first material piece to a first application station and applying said first material piece to a first portion of said absorbent product web, said first portion being located at a first end portion of at least one absorbent product of said absorbent product web; and
feeding said second material piece to a second application station and applying a section of said second material piece having the aperture therein in a stretched condition to a second portion of said absorbent product web, said second portion being located at a second end portion of at least one absorbent product of said absorbent product web.

\* \* \* \* \*